United States Patent [19]

Dufresne et al.

[11] Patent Number: 5,607,402
[45] Date of Patent: Mar. 4, 1997

[54] PRE-ASSEMBLED SAFETY NEEDLE HOLDER

[75] Inventors: Christopher Dufresne, Jarrie; Patrice Mousset, Varces, both of France

[73] Assignee: Becton Dickinson and Company, Franklin Lakes, N.J.

[21] Appl. No.: 308,231

[22] Filed: Sep. 19, 1994

[30] Foreign Application Priority Data

Aug. 18, 1994 [EP] European Pat. Off. .............. 94112893

[51] Int. Cl.$^6$ ...................................................... A61M 5/00
[52] U.S. Cl. ........................... 604/263; 604/198; 604/110
[58] Field of Search ...................................... 604/263, 110, 604/187, 192, 198; 128/763, 765, 919

[56] References Cited

U.S. PATENT DOCUMENTS

| | | | |
|---|---|---|---|
| 4,723,943 | 2/1988 | Spencer | 604/198 |
| 4,767,413 | 8/1988 | Haber et al. | 604/198 |
| 4,923,447 | 5/1990 | Morgan | 604/198 |
| 4,994,045 | 2/1991 | Ranford | 604/198 |
| 5,067,490 | 11/1991 | Haber | 128/763 |
| 5,070,885 | 12/1991 | Bonaldo | 128/763 |
| 5,120,311 | 6/1992 | Sagstetter et al. | 604/110 |
| 5,171,231 | 12/1992 | Heiliger | 604/263 |
| 5,222,947 | 6/1993 | D'Amico | 604/198 |
| 5,267,977 | 12/1993 | Feeney, Jr. | 604/198 |
| 5,306,258 | 4/1994 | de la Fuente | 604/198 |
| 5,332,092 | 7/1994 | Fischer | 206/365 |
| 5,383,863 | 1/1995 | Mardones | 604/198 |
| 5,498,245 | 3/1996 | Whisson | 604/198 |
| 5,501,672 | 3/1996 | Firth et al. | 604/177 |
| 5,514,107 | 5/1996 | Haber et al. | 604/197 |

Primary Examiner—Corrine M. McDermott
Assistant Examiner—V. Alexander
Attorney, Agent, or Firm—Alan W. Fiedler

[57] ABSTRACT

A safety needle holder (2) includes a tubular housing (4) as well as a double-ended cannula (16) mounted within the housing (4) for slidably moving between an extended distal position, wherein the cannula (16) projects from the housing (4) and is exposed, e.g., for drawing blood, and a retracted proximal position, wherein the cannula (16) is safely located within the housing (4). An intermediate, pre-assembled position is provided between said distal and proximal positions, wherein the cannula (16) is located during assembly of the needle holder (2).

10 Claims, 4 Drawing Sheets

PRE-ASSEMBLED SAFETY NEEDLE HOLDER

BACKGROUND OF THE INVENTION

The present invention relates to safety needle holders of the kind currently used i.a. in intravenous access devices such as disposable blood collection devices.

Such a needle holder is known, for instance from U.S. Pat. No. 5,067,490, U.S. Pat. No. 5,070,885 and FR-A-2 686 242.

U.S. Pat. No. 5,067,490 discloses a shielded safety syringe comprising a cylindrical outer sleeve and an inner needle carrier holding a double-pointed needle in fluid communication with a vacuum tube and slidable within the outer sleeve between two positions. In the first, distal position, the needle projects from the outer sleeve and is exposed for drawing blood. In the second, proximal position, the needle is retracted within the outer sleeve. The needle carrier is releasably held in the first position, so that it can be readily moved into the second position after use. After the needle has been retracted into the sleeve, the carrier is locked in its second position to prevent health care workers from coming into accidental contact with the used needle.

The arrangement disclosed in U.S. Pat. No. 5,070,885 provides for a double-ended cannula to be retracted within a respective sleeve or barrel for storage and disposal. The cannula is attached to the device immediately prior to use by being threaded into an aperture formed in a movable disc disposed within the barrel and rotated to a locked operating distal position for attachment to the cannula and use. After use, the disc is counter-rotated to permit the cannula, mounted onto the disc, to be longitudinally retracted completely within the barrel to a proximal position in which the cannula is permanently locked by stopping the disc against further movement.

Again, the device disclosed in FF-A-2 686 242 comprises an outer, tubular housing, wherein a double-ended cannula or needle is located for longitudinal axial sliding movement with respect to the housing. Specifically, the double-ended needle is mounted onto a needle carrier having a formation protruding in such a way to be accessible from outside the housing. The needle carrier, as well as the needle mounted thereon, is slidable within the housing between a first distal position, wherein the needle projects from the housing and is exposed (e.g. for drawing blood) and a second, retracted proximal position, wherein the needle is safely located within the housing.

A basic common disadvantage to all the "two-position" arrangements considered in the foregoing is due to the fact that they generally require the needle to be a separate part of the whole arrangement, which should be generally packaged separately under sterile conditions and then assembled onto the holder just prior to use.

Consequently, the need exists of providing such a holder, wherein the needle can be pre-assembled by the manufacturer, thus dispensing with the need for the user of obtaining a new needle, removing any needle sterility caps or similar arrangements and finally screwing the needle onto the holder.

The underlying problem of the invention is to provide an improved safety needle holder fully satisfying that need.

SUMMARY OF THE INVENTION

In brief, the needle holder according to the invention is designed in such a way as to allow pre-assembly of, e.g., a double-ended blood collection needle by the manufacturer. This is achieved by providing between the distal position, wherein the needle projects from the housing and is exposed for use (e.g. for drawing blood) and the proximal, retracted safety position, an intermediate pre-assembled position, wherein the needle carrier is located during assembly of the needle holder. In use, the needle carrier can be displaced with a minimal force from the intermediate pre-assembled position to be pushed forward to the distal exposed position. Once the blood drawing operation or the like is completed, the needle carrier can be withdrawn over the intermediate pre-assembled position to reach the retracted safety position.

The intermediate pre-assembled position is therefore designed to hold the needle before use while allowing easy disengagement for blood access, without interfering with retraction of the needle into the holder housing to its secure position after use.

The invention also relates to a safety needle holder package including a safety needle holder as defined in the foregoing.

BRIEF DESCRIPTION OF THE DRAWINGS

The invention will now be described, by way of example only, with reference to the enclosed drawings, wherein.

DETAILED DESCRIPTION OF THE INVENTION

Figure 1:
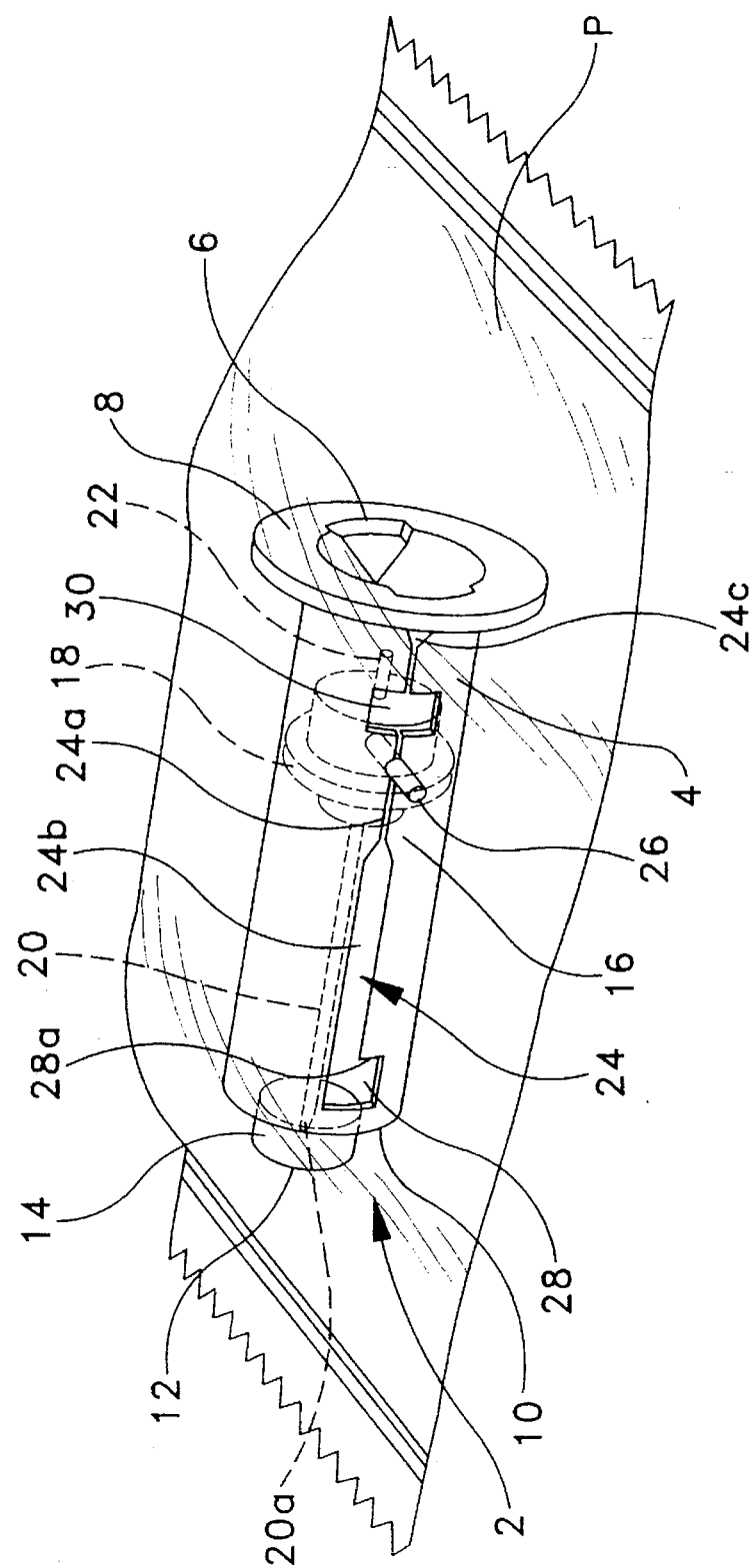
FIGS. 1–3 show schematically a safety needle holder according to the present invention in three different positions during use.

Referring to the drawings, a safety needle holder 2 in accordance with the present invention generally comprises an outer, tubular housing 4 having an open end 6 and a radially outwardly extending flange 8 at that end. The housing 4 defines a cylindrical sleeve or barrel which extends to another end of the housing, which in turn is closed by a transverse end wall 10. A coaxial aperture 12 is formed within a central boss 14, provided on the outer surface of the end wall 10.

The housing 4 is composed of a material adapted for use in a medical environment, such as moulded medical grade polypropylene or the like. Use of materials showing at least a certain degree of flexibility, is preferred for reasons explained in detail in the following.

A needle member in the form of a double-ended cannula 16 is mounted within the housing 4 by means of a carrier, typically in the form of a disc 18, through which the cannula 16 extends so as to be axially aligned with the housing 4. The carrier 18 is mounted onto the cannula 16 so that a first blood collecting needle 20, having a sharp puncturing tip 20*a*, may be extended through the aperture 12 by movement of the carrier 18 towards the closed end 10 to the disposition shown in FIGS. 2 and 6 and may be retracted to the disposition shown in FIGS. 3 and 7 by movement of the carrier 18 away from the closed end 10 and towards the open end 8 of the housing 4.

Opposite the blood-collecting needle 20, the double-ended cannula 16 has a sample transfer needle 22 which is used in a conventional fashion to transfer the blood from the patient through the collecting needle 20 into an evacuated sample collection container of conventional configuration (not shown). Such sample collection containers are well-known in the art and are sold, for example, under the trademark VACUTAINER by the assignee of the instant application. Additional details of manufacturing the housing 4, the double-ended cannula 16 and the carrier 18 are well-known in the art as witnessed, e.g., by the devices sold as SAFETY-GARD needle holder and VACUTAINER needles by the same assignee.

In the embodiment preferred at present, the housing 4 has a circular cross-section with a longitudinal passage and, most preferably, two diametrically opposed longitudinal passages 24 extending axially through the wall of the housing 4 in order to form each a guiding slot for a respective boss 26 extending radially from the carrier 18 to act as an actuation element for the carrier 18.

In a manner known per se, the or each guiding boss 26 extends radially from the carrier 18 through the respective slot 24 in the housing wall to a sufficient length to permit engagement thereof by one finger (typically the thumb) of a user handling the holder 2.

It will be appreciated that the presence of a single slot 24 for sliding engagement by a respective radial boss 26 extending from the carrier 18 will generally suffice to enable the user to control sliding movement of the needle carrier 18 (and the cannula 16) along the housing 4. Nevertheless, the presence of at least two diametrically opposed slots 24, wherein two respective, diametrically opposed radial bosses of the carrier 18 slidably engage, is advantageous both for safely retaining central axial alignment of the cannula 16 with respect to the housing 4 and for permitting the user to find promptly a position for controlling movement of the carrier 18 and the cannula 16 acting on either boss 26 without having to turn appreciably the housing 4 around its longitudinal axis once grasped for use. Consequently, in the following two slots 24 and two bosses 26 will be referred to.

Figure 2:
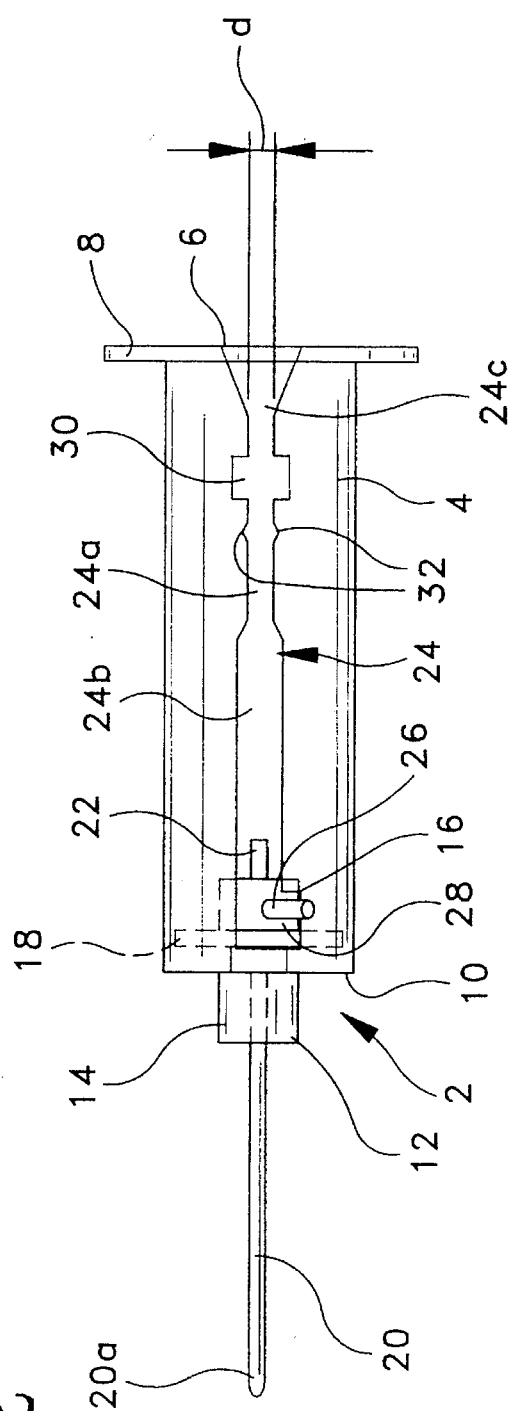
Figure 3:
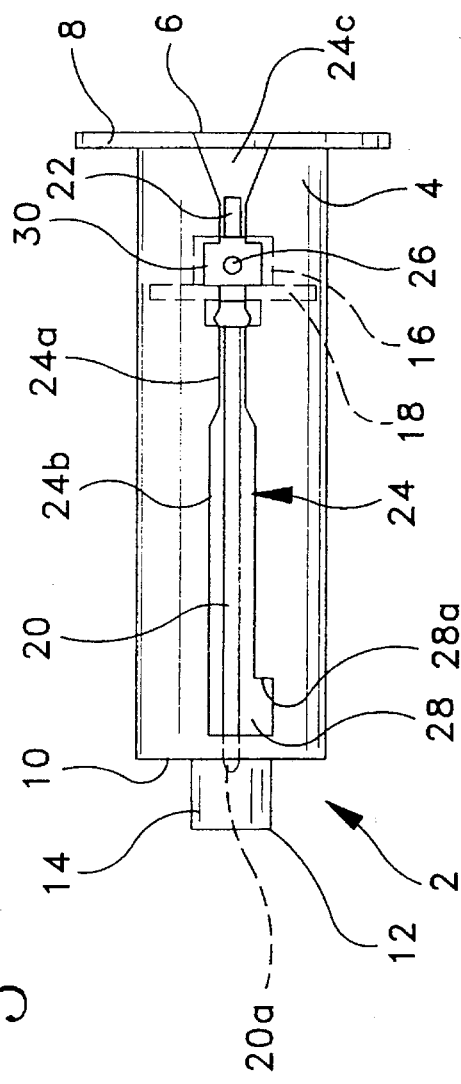

In the embodiment to which FIGS. 1–3 refer, each longitudinal slot 24 essentially includes:

an intermediate, neck portion 24a located approximately a ⅓ of the overall housing length starting from the open end 6, an enlarged forward portion 24b, terminating into an enlarged, off-axis opening or window 28 in the housing wall, adjacent to the closed end 10 of the housing 4, a further back opening or window 30 located between the intermediate neck portion 24a and the open end 6 of the housing 4, and a terminal, flared portion 24c connecting the second window 30 with the open end 6 of the housing 4.

The side walls defining the intermediate neck portion 24a are separated by a distance (designated d and expressly indicated in FIG. 2 only) and include at least one and preferably two opposed notches 32 for gently yet securely holding the respective radial boss 26 by a pinching action due to the general resilient nature of the material comprising the housing 4.

Figure 4:
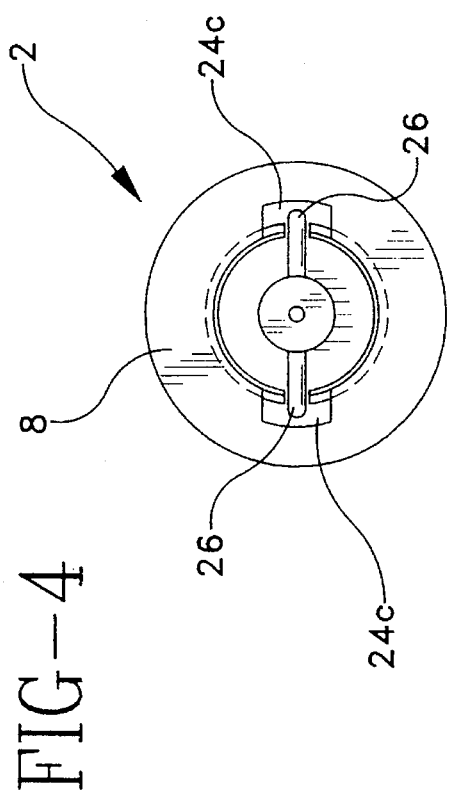
FIG. 4 is a cross-sectional view taken along line IV—IV of FIG. 1, and FIGS. 5–7 show an alternative embodiment of a needle holder according to the invention in three different positions during use.

Upon assembly of the holder 2, the needle carrier 18, having the cannula 16 mounted thereon, is inserted into the housing 4 starting from the open end thereof by causing radial bosses 26 to pass through the flared end portions 24c of slots 24 (which extend axially through flange 8—see FIG. 4) then through the windows 30 onto the pre-assembled position in the neck portion 24a as shown in FIG. 1, where bosses 26 are retained in the notches 32.

Preferably, the flared portion 24c is comprised of a outermost wedge-shaped portion facilitating centering of the bosses 26 and—consequently—of the carrier 18 and the cannula 16 during insertion into the housing 4 and a innermost restricted portion whose width d is equal to that of neck portion 24a, d being chosen in such a way that both portions 24a and 24c are slightly narrower than the corresponding radial dimension of bosses 26, thereby preventing undesired axial sliding of the carrier 18 along the housing 4 when bosses 26 engage either of portions 24a and 24c.

Once the needle holder is assembled (pre-assembled) in the disposition shown in FIG. 1, which can be carried out by automatic means (known per se), it can be subjected to sterilization treatment and packaged under sterile conditions, e.g., in an envelope for example of the flow-pack type (designated P and shown schematically in FIG. 1 only) in view of storage and delivery to the end user.

To use the holder of the invention as a blood collection tube holder, a laboratory technician takes the holder 2 from its sterile package and then holds the holder 2 in the pre-assembled disposition shown in FIG. 1. Holding the housing 4, the technician acts with his thumb on the end of either boss 26 extending radially outwardly of the housing 4 through the respective slot 24 to extend the needle 20 out of housing 4 by causing the tip 20a to pass through the aperture 12 of the closed end 10 to pierce a patient's skin to extend it into a vein.

While continuing to hold the housing 4 with one hand, the technician inserts an unused previously collection tube (not shown) into the open end 6 of the housing 4. As the tube is pushed against the protruding proximal needle end 22, a protective sheeting is first pierced by the needle 22 which then pierces through an evacuated collection tube and plug.

As best shown in FIG. 2, the general off-axis location of the window 28 enables the user to rotate slightly the needle carrier 18 acting on bosses 26, thereby causing them to abut against the shoulder wall (designated 28a) formed on the side of the window 28 opposed the closed end 10.

Under these conditions, the cannula 16, and specifically the distal needle end extending out of a the housing 4, is securely maintained into its extended distal position. Blood now flows from the vein through the needle into the vacuum tube.

When sufficient blood has been drawn, the technician separates the vacuum tube from the holder 2 by pulling on the tube with one hand, while holding the housing 4 with the other hand, whereby the vacuum tube automatically reseals itself (in a manner known per se) after disengagement from the needle 22.

If additional blood samples are required, the technician will repeat the above-summarized procedure to attach further, unused evacuated collection tubes to the holder 2 and thereby draw additional blood samples.

After the last sample has been drawn, the used needle 20 may be retracted by slightly counter-rotating the carrier 18 acting on bosses 26 to re-align them axially with slots 24 and then sliding the carrier 18 relative to the housing 4 axially towards the open end 6 until the distal needle end 24a is fully retracted within the housing 4. This is safely achieved, once the carrier 18 reaches its proximal position with the bosses 26 extending through the respective back windows 30.

The suitable choice of the depth of notch or notches 32 in relation with the pinching force due to the thickness and resilience of the material comprising the wall of the housing 4 will enable the technician to move the carrier 18 from the distal position of FIG. 2 back to the retracted proximal safety position of FIG. 3 over the intermediate, pre-assembled position of FIG. 1 without any appreciable effort.

Once the bosses 26 have reached the windows 30, the carrier 18 will be safely prevented from being inadvertently pushed back to the distal position of use, as this could only be obtained by exactly centering the bosses 26 with respect to slots 24 and by pushing again the carrier 18 forward along the housing 2 against the friction force exerted by the side wall of the neck portion 24a of the slots 24 against the bosses 26. Also, the carrier 18 will be in any case prevented from further sliding towards the open end 6 due to friction of the bosses 26 against the side walls of the restricted part of the flared portions 24c.

Figure 5:
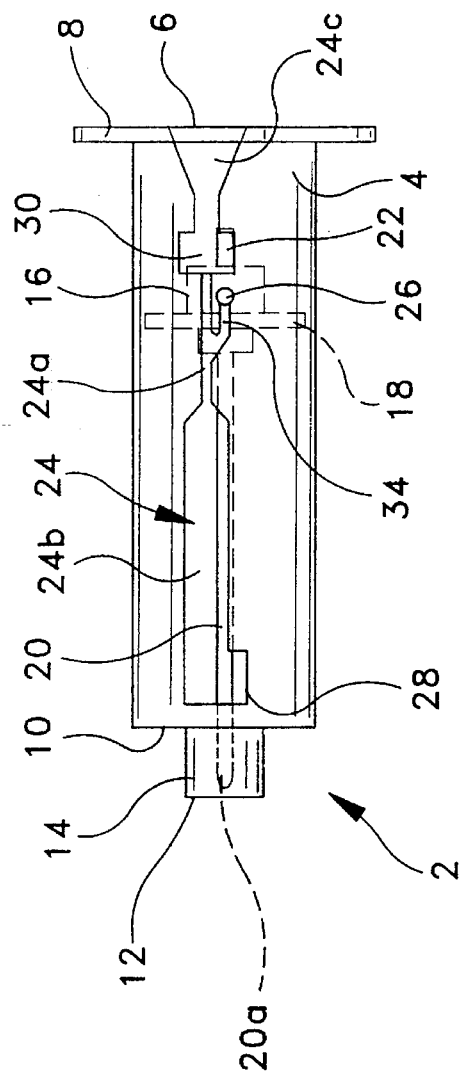
Figure 6:
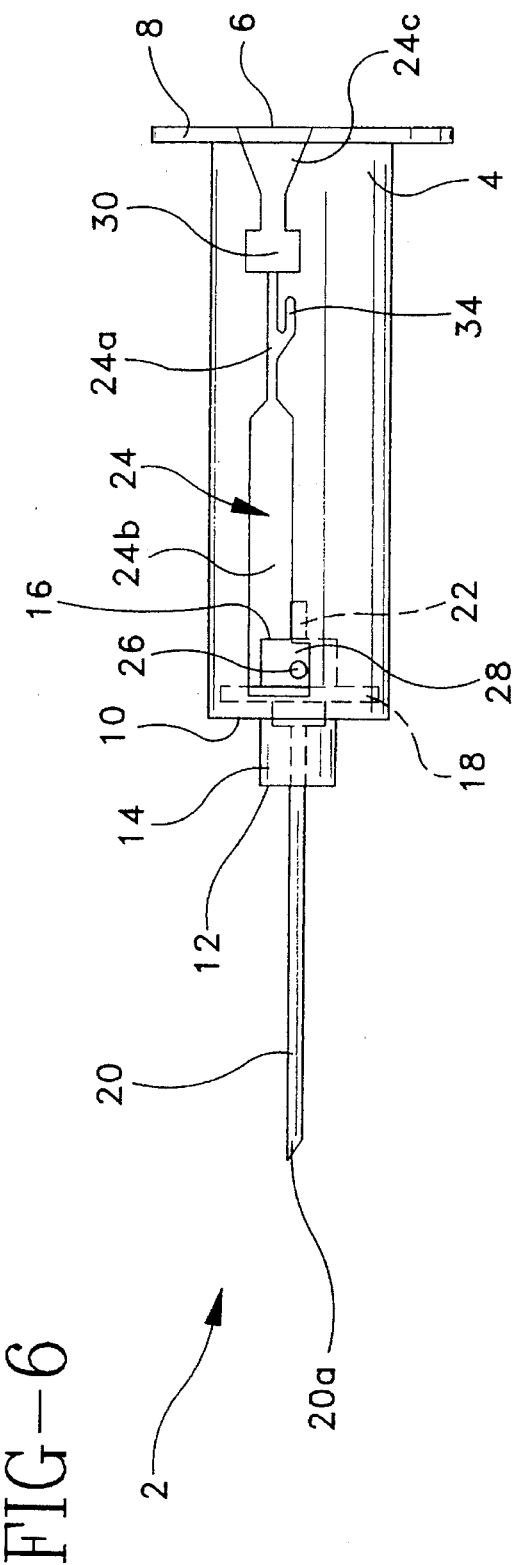
Figure 7:
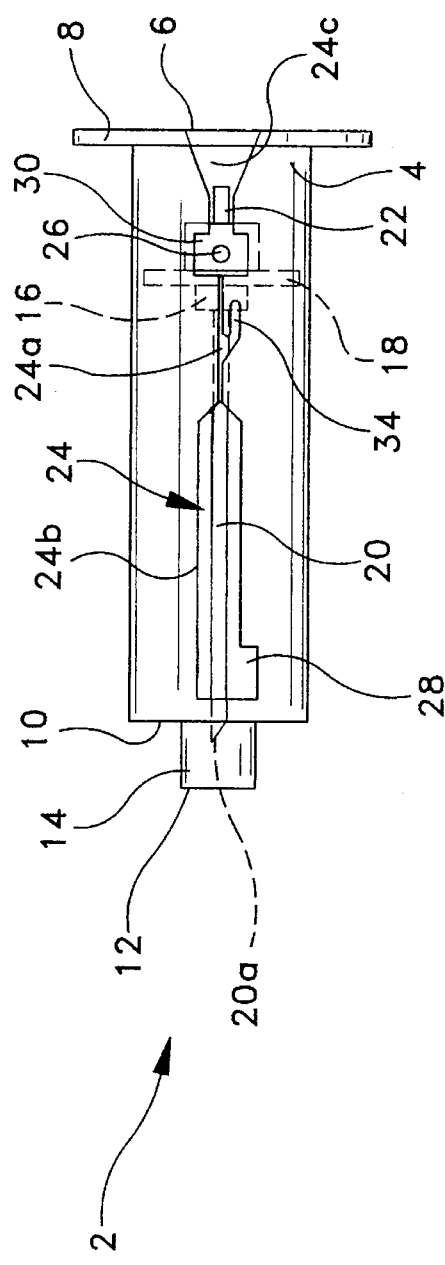

Structure and operation of the alternative embodiment shown in FIGS. 5–7 is essentially as explained in the foregoing, whereby the same reference numerals appearing in FIGS. 1–4 were used in FIGS. 5–7 to designate corresponding or like parts.

The basic difference between the embodiment of FIGS. 1–4 and the embodiment of FIGS. 5–7 lies in the different arrangement resorted to for ensuring the intermediate, pre-assembled position.

In the embodiment of FIGS. 5–7, bosses 26 are retained in the intermediate pre-assembled position by engaging a lateral, dead-end 34 arm of the intermediate neck portion 24a of the respective slots 24, where bosses 26 are gently retained by friction against the side walls of said dead-end arm 34.

In this alternative embodiment, the carrier 18 is pushed towards its distal position (passing from the disposition shown in FIG. 5 to the disposition shown in FIG. 6) by causing each boss 26 to slide along the dead-end arm 34 onto the neck portion 24a, the portion 24b and the window 28 of the respective slot 24.

The subsequent withdrawal sliding movement of the carrier 18 towards the proximal safety position is performed as explained in connection with the embodiment of FIGS. 1–4 by causing bosses 26 to slide back along the slots 24 until the back windows 30 are reached. The embodiment of FIGS. 5–7 provides the additional advantage due to the fact that, contrary to the embodiment of FIGS. 1–4, the intermediate pre-assembled position is not to be passed over during the withdrawal movement of the carrier 18. Such withdrawal movement can thus be made even more regular and easy to perform than in the case of the embodiment of FIGS. 1–4.

Variations and modifications can be made to the present invention without departing from the scope thereof. For example, as an alternative to the notch arrangement designated 32 or the dead-end arm 34, other retention members or means for retaining the carrier 18 and the cannula 16 in the intermediate, pre-assembled position of FIGS. 1 and 5 can be devised.

We claim:

1. A safety needle holder including:

a housing;

a needle member slidably mounted within said housing for movement between three predetermined different positions in said housing including:

an extended distal position, wherein said needle member projects from said housing;

a retracted proximal position, wherein said needle member is safely located and locked within said housing; and an initial pre-assembled position located between said extended distal position and said retracted proximal position, wherein said needle member is securely held within said housing prior to use;

retention means in said housing for securely holding said needle member in said initial pre-assembled position; and at least one actuation element on said needle member for selectively pushing said needle member from said initial pre-assembled position to said extended distal position and then back to said retracted proximal position.

2. A safety needle holder according to claim 1, wherein said housing includes a tubular sleeve having at least one axial slot with side walls for slidably receiving said at least one actuation element on said needle member.

3. A safety needle holder according to claim 2, wherein said retention means further includes at least one notch in the side walls of said at least one axial slot.

4. A safety needle holder according to claim 2, wherein said at least one axial slot has a lateral arm extending therefrom to retain said at least one actuation element on said needle member in said pre-assembled position.

5. A safety needle holder according to claim 2, wherein said retention means is located at an intermediate neck portion of said at least one slot.

6. A safety needle holder according to claim 2, wherein said at least one axial slot includes first and second windows located at opposite ends of said slot to receive said at least one actuation element in said distal and proximal positions, respectively.

7. A safety needle holder according to claim 6, wherein said first window is located off-axis with respect to said at least one axial slot to enable rotation of said needle member to lock said needle member into said distal position.

8. A safety needle holder according to claim 6, wherein said tubular sleeve includes an open end adjacent said second window and said at least one axial slot extends to said open end over said second window by means of a terminal flared portion to form a wedge-like insertion path for said at least one actuation element into said sleeve.

9. A safety needle holder according to claim 1, wherein said needle member further includes a needle carrier slidably mounted within said housing and provided with at least one boss radially protruding from said carrier to form said actuation element on the needle member.

10. A safety needle holder according to claim 9, wherein said housing includes a tubular sleeve having at least one axial slot with side walls for slidably receiving said at least one actuation element on said needle member and wherein said tubular sleeve is comprised of a flexible material and the width (d) of said one axial slot is at least locally selected relative to the dimensions of said at least one boss to pinch said one boss for gently retaining said needle member in said pre-assembled position.

* * * * *